United States Patent [19]

Huang et al.

[11] Patent Number: 5,612,186
[45] Date of Patent: Mar. 18, 1997

[54] **ENZYME-CAPTURE ASSAY (ECA) FOR THE IDENTIFICATION OF *ESCHERICHIA COLI* IN CLINICAL SAMPLES**

[75] Inventors: Shiu W. Huang, Hsinchu; Jiunn J. Wu, Tainan; Tsung C. Chang, Taoyuan, all of Taiwan

[73] Assignee: Food Industry Research and Development Institute, Taiwan

[21] Appl. No.: 263,541

[22] Filed: Jun. 22, 1994

[51] Int. Cl.$^6$ ............................................. G01N 33/569
[52] U.S. Cl. ...................... 435/7.37; 435/7.4; 435/7.92
[58] Field of Search ............................ 435/7.2, 7.32, 435/7.37, 7.4, 34, 7.92

[56] References Cited

U.S. PATENT DOCUMENTS 5,268,463  12/1993  Jefferson .

OTHER PUBLICATIONS

S.M. Holt et al., "Enzyme–Capture Assay for Rapid Detection of *Escherichia coli* in Oysters", Applied and Environmental Microbiology, Inc. vol. 55:229 (1989).

M.O. Husson et al., "Alkaline Phosphatase Capture Test for the Rapid Identification of *Escherichia coli* and Shigella Species Based on a Specific Monoclonal Antibody" Jour. of Clinical Microbiology, vol. 27:1518 (1989).

Shiu Wen Huang et al., "Enzyme Capture Assay for Rapid Identification of *Escherichia coli* in Blood Cultures", Journal of Clinical Microbiology, vol. 32:1444, (1994).

Shiu Wen Huang et al., "A Rapid Method for the Detection of *Escherichia coli*–Enzyme Capture Assay", (1993).

Frampton, E. W. et al. "Methods for *Escherichia coli* identification in food, water and clinical samples based on beta–glucuronidase detection." *Journal of Applied Bacteriology*, vol. 74 (1993), pp. 223–233.

Kasper, C. W. et al. "Coagglutination and Enzyme Capture Tests for Detection of *Escherichic coli* beta–galactosidase, beta–glucuronidase, and glutamate decarboxylase." *Applied and Environmental Microbiology*, vol. 53 (May 1987), pp. 1073–1077.

*Primary Examiner*—James C. Housel
*Assistant Examiner*—Rachel Heather Freed
*Attorney, Agent, or Firm*—Fish & Richardson P.C.

[57] ABSTRACT

An enzyme-capture assay (ECA) for rapid identification of *Escherichia coli* (*E. coli*) in clinical samples comprising contacting a clinical sample which is suspected to contain *E. coli* with an immobilized antibody against β-D-glucuronidase which then catalyzes an enzyme substrate to produce a fluorescent product is disclosed.

9 Claims, 2 Drawing Sheets

ENZYME-CAPTURE ASSAY (ECA) FOR THE IDENTIFICATION OF *ESCHERICHIA COLI* IN CLINICAL SAMPLES

BACKGROUND OF THE INVENTION

The isolation of any significant microorganism from a blood culture is an occurrence that requires careful evaluation by clinicians, and prompt action is usually necessary. The incidence of bacteremia and fungemia had been reported to be 3.4–28/1,000 hospital admissions and was estimated to average 10/1,000 (1%) in the United States (1). The five common isolates from blood cultures were *Escherichia coli* (*E. coli*), *Staphylococcus aureus*, *Streptococcus pneumoniae*, *Klebsiella pneumoniae*, and *Pseudomonas aeruginosa* (2). *E. coli* is the most important gram-negative bacterium in clinical microbiology laboratories. It is isolated frequently from bacteremic episodes (2, 3, 4, 5, 6), either as a pure culture or as part of a mixed culture. The isolation rate of *E. coli* can be as high as 40% among the gram-negative bacteria found in bacteremia (6). During the period 1991–1992, in one of the inventors' hospital (National Cheng-Kung University Hospital, Tainan, Taiwan), isolates of *E. coli* accounted for 21.7% of all bacteria causing bloodstream infections (unpublished data). In another study, *E. coli* is responsible for 28.4% of all isolates from bacteremic episodes in the pediatric department (7). In view of the high incidence and mortality rate (2), a rapid identification method of *E. coli* in blood specimens is of clinical importance.

The common practice used in hospitals to identify *E. coli* is to subculture blood specimens at intervals after an incubation period of 12 hours to 2 weeks (3, 8), and at the time when Gram stain is positive or bacterial growth is apparent (e.g. turbidity, gas production or hemolysis). The subculture and identification steps, however, normally take at least 24 hours. In view of the high incidence and high mortality rate of bacteremia caused by *E. coli*, in addition to the conventional culture protocols, it is plausible, when the growth of gram-negative bacteria is found, to parallelly perform specific assays to rapidly identify *E. coli* in blood cultures so that relevant treatment can be started earlier than the conventional identification systems.

Since Kilian and Bülow (9) described the activity of a β-D-glucuronidase (GUD) in restricted species belonging to Escherichia, Shigella, and Salmonella in 1976, this property has been widely used for the detection and identification of *E. coli* (10, 11, 12, 13, 14) in the food and clinical microbiology laboratories. Most reports incorporated 4-methylumbelliferyl-β-D-glucuronide (MUG) as a fluorogenic substrate of GUD in the media. Some other bacteria (Yersinia, Flavobacterium, staphylococci, and streptococci) are also positive for this enzyme (15, 16, 17), and false-positive reactions are sometimes caused by the animal tissues which contain the enzyme. For this reason, an enzyme-capture assay (ECA) for detection of *E. coli* in oysters was developed (15). Anti-GUD antibodies coated on the microtiter plate were used to capture the enzyme produced by *E. coli* present in the food samples, followed by the addition of fluorogenic or chromogenic substrates to demonstrate the GUD activities. Under this condition, cross-reactions are only caused by the members of Enterobacteriaceae.

Although the direct incorporation of a fluorogenic substrate of GUD into a culture media is a convenient and fast way to detect *E. coli* present in specimens, the practice is impossible for blood cultures, due to the deep red color of blood which masks the fluorescence generated by GUD on the substrate. Enzyme-capture assay seems to be a good choice for solving this problem.

Recently, Husson et al. (18) have described an alkaline phosphatase capture test for the identification of *E. coli* and Shigella species in blood cultures and urine specimens. Although the specificity (96.8%) is high for detecting *E. coli* from urine specimens, the sensitivity is relatively low (91%) for blood cultures.

It is still in grave need to develop a rapid method for identifying *E. coli* in clinical samples with sufficiently high sensitivity and specificity to ensure earlier commencement of antimicrobial treatments.

SUMMARY OF THE INVENTION

It is therefore an object of the invention to provide a rapid enzyme-capture assay (ECA) for identifying *E. coli* in clinical samples with sufficiently high sensitivity and specificity.

The object, advantages and features of the present invention will be more fully understood and appreciated by reference to the written specification.

DETAILED DESCRIPTION OF THE INVENTION

Figure 1:
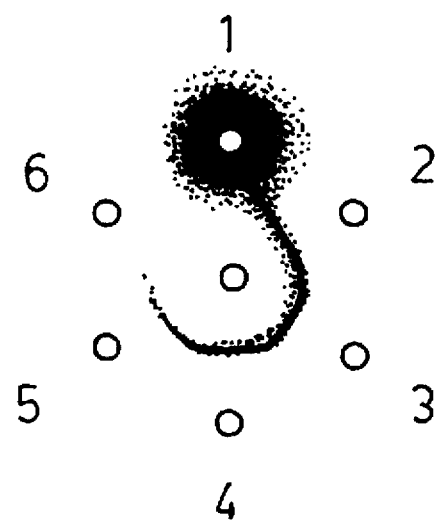
FIG. 1 shows the specificity of the β-D-glucuronidase (GUD) antisera determined by Ouchterlony double diffusion test. The sample in the central hole of the figure is GUD (1 mg/ml). The antisera diluted 1×, 2×, 4×, 8× and 16×, respectively, were put clockwise into holes 2–6. Hole 1 contains normal rabbit serum.
Figure 2:
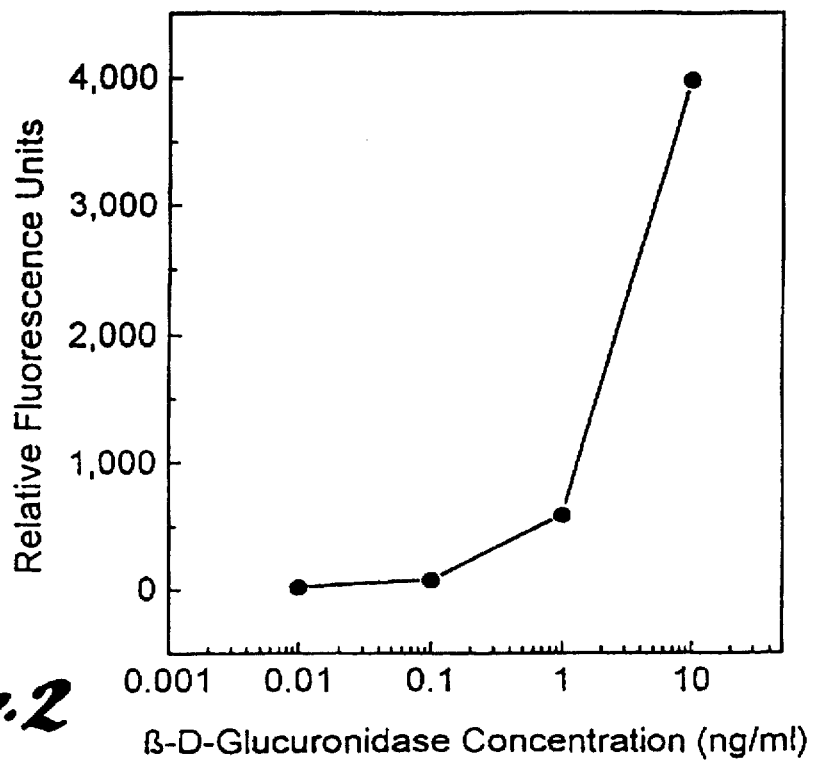
FIG. 2 shows the dose response of enzyme-capture assay for β-D-glucurondiase (GUD). The microtiter plate was coated with affinity-purified anti-GUD and 4-methylumbelliferyl-β-D-glucuronide (MUG) was used as a fluorogenic substrate of the enzyme. Each point represents mean of duplicates. The negative control had a relative fluorescence units of 15.

We have now found that the object of the invention can be fulfilled by an enzyme-capture assay (ECA) utilizing β-D-glucuronidase (GUD) as a marker of *E. coli*.

Thus, the method in accordance with the invention comprises contacting a clinical specimen which is suspected to contain *E. coli* with an antibody against GUD, and the activity of the captured enzyme is revealed in the presence of a fluorogenic substrate. Specifically, if *E. coli* is present in a blood specimen which shows growth of gram-negative bacteria, the antibody against GUD will capture the GUD produced by *E. coli* in the specimen and the enzyme can hydrolyze the fluorogenic substrate to generate a fluorescence, demonstrating the presence of E. coli.

The time required for carrying out the present method is 4 hours. Therefore, in comparison with the conventional subculture and identification methods, the method of the invention allows specific antimicrobial treatment to be started 24 hours earlier than other commonly used systems, and may help to reduce the mortality rate of bacteremia caused by E. coli.

The antibody used in the method of the invention can be either a monoclonal antibody or a polyclonal antibody if the specificity of the antibody is high enough to specifically capture the β-D-glucuronidase produced by E. coli in a clinical sample. The method for preparing an antibody with high specificity is well known to those skilled in the art. For instance, a procedure of preparative gel electrophoresis followed by activity stain (10) can be used to purify GUD from commercial crude preparations of the enzyme, and the purified GUD can be directly used for immunizing animals to obtain specific antibodies against GUD. In this manner, a highly purified GUD can be obtained and injected into rabbits within two days. Another advantage of using polyacrylamide gel containing GUD to immunize animals is that the gel itself was reported to have the same effect as an adjuvant (19). Therefore, the activity stain technique (zymogram) on electrophoresis gels is a rapid and convenient way to obtain pure GUD for immunization purpose.

In an embodiment of the invention, a procedure of preparative gel electrophoresis followed by activity stain was used to purify partially purified GUD from E. coli K-12. The blue band (due to the cleavage of indolyl-β-D-glucuronide by GUD to form insoluble indigo) corresponding to GUD was cut from the electrophoresis gels and after a grinding step, the gel was used for immunization of New Zealand white rabbits. After priming and 4 booster injections the titers of the antisera from rabbits were found to be around $10^7$ as determined by an enzyme-linked immunosorbent sassy. The antisera were specific to GUD and can be advantageously utilized in the method of the invention.

Various substrates can be used in the method in accordance with the invention. For instance, 4-methylumbelliferyl-β-D-glucuronide (MUG) is one of the fluorogenic substrates applicable to the method of the invention. In an embodiment of the invention using MUG as the fluorogenic substrate, the detection limit was 0.1 ng/ml ($3\times10^{-13}$M) of the enzyme, which is approximately equal to a cell concentration of $10^6$ CFU/ml of E. coli.

Several workers (9, 15) have previously noted that some strains of Shigella and Salmonella also can produce GUD. However, only a small percentage of bloodstream infections is caused by Salmonella, and bacteremia caused by Shigella is rarely found (1, 3, 4, 6, 20). Among the 212 positive blood cultures found in the study in accordance with the invention, Salmonella were found in only five (3%) specimens, and only one of the five samples displayed ECA-positive result. No Shigella were isolated from the 212 positive blood samples. Therefore, the chances of false-positive reaction caused by Shigella or Salmonella in blood cultures would be very low.

Besides, it is known that GUD is an inducible enzyme (21). To reduce the false-negative reactions under the condition when competitive microbes or residual antibiotics are present in the blood specimens, appropriate inducers can be incorporated into the blood culture to enhance the production of GUD by E. coli. Suitable inducers applicable to the method in accordance with the invention include β-D-glucuronide derivatives. Preferably, the inducers can be one of the following compounds: 5-bromo-4-chloro-3-indolyl-β-D-glucuronide, methyl-β-D-glucuronide, 4-methyl-umbelliferyl-β-D-glucuronide and p-nitrophenyl-β-D-glucuronide or the combination thereof. More preferably, the inducer is p-nitrophenyl-β-D-glucuronide. In an embodiment of the invention utilizing p-nitrophenyl-β-D-glucuronide (50 μg/ml) as an inducer, the detection limit of E. coli was one order lower ($10^5$ CFU/ml).

The clinical samples to be analyzed in accordance with the invention can be collected in a conventional manner. The definition of clinical samples is well known in the art and may include e.g. blood samples and urine samples.

Finally, the method of the invention can be practiced in a variety of ways. For instance, the anti-glucuronidase can be coated on microtiter plates or microbeads or particles to capture the enzyme. The utilization of microtiter plates has the advantage of automation. Thus, in a preferred embodiment in accordance with the invention, the anti-glucuronidase was coated on microtiter plates.

The invention will be more understood from the description of the following non-limiting examples.

EXAMPLES

Bacterial Strains and Culture Conditions

Among the 108 stock cultures of E. coli tested for the production of GUD by ECA, 102 were clinical isolates obtained from the Triservice General Hospital (Taipei, Taiwan). The remaining 6 strains of E. coli and other 60 strains of Enterobacteriaceae were from the Culture Collection and Research Center (CCRC, Hsinchu, Taiwan). The identity of all E. coli isolates was reconfirmed by the Micro-ID diagnostic kit (Organon Teknika Corp., Durham, N.C., USA). To test the production of GUD, one single colony of overnight culture of each strain-grown overnight on tryptic soy agar was suspended in 0.5 ml of sterile saline. Following the injection (with a syringe) of the bacterial suspension into the BACTEC NR6A (Becton Dickinson, Sparks, Md., USA) aerobic blood culture vial, 3 ml of human blood (from healthy donors) was added to the culture bottle. This was to test the production of GUD by different bacteria under a growth environment similar to the routine cultivation condition of blood samples. The blood culture bottles were incubated at 35° C. for 24 hours before performing the ECA.

Among the 108 strains of E. coli tested, 104 (96.3%) produced GUD as detected by ECA (Table 1). One quarter (25%) of Shigella spp. and two strains (7%) of Salmonella also gave positive ECA results. Of the other 24 strains of Enterobacteriaceae tested, none produced GUD as determined by ECA.

TABLE 1

Production of β-D-glucuronidase (GUD) by 168 strains of Enterobacteriaceae. The presence of GUD was analyzed by an enzyme-capture assay (ECA)

| Organism | No. of strains tested | No. (%) of strains ECA-positve |
|---|---|---|
| Escherichia coli | 108 | 104(96.3) |
| Salmonella spp. | 28 | 2(7) |
| Shigella spp. | 8 | 2(25) |
| Citrobacter spp. | 3 | 0 |
| Enterobacter spp. | 2 | 0 |
| Klebsiella spp. | 7 | 0 |
| Proteus spp. | 11 | 0 |
| Serratia sp. | 1 | 0 |

Purification of GUD

Partially purified GUD from E. coli K-12 (Boehringer Mannheim, Germany) was further purified by disc polyacrylamide gel (10%, 3-mm thick) electrophoresis using a vertical apparatus (Model V16, Bethesda Research Laboratory, Bethesda, Md., USA). The crude enzyme solution (1.2 ml) was loaded on top of the disc gel (without a comb) and electrophoresed at 4° C. After electrophoresis, the gel was activity-stained with the chromogenic substrate 5-bromo-4-chloro-3-indolyl-β-D-glucuronide (Sigma, St. Louis, Mo., USA; 50 µg/ml) dissolved in 0.2M phosphate buffer, pH 6.5. After 10 to 15 min incubation at room temperature, the blue band (10) corresponding to the position of GUD was visible. The band was cut from the gel by a razor and used for antibody production.

Preparation and Purification of Antibody

The gel strip containing GUD was cut into small pieces and ground to fine particles with a hand homogenizer. The crushed gel containing about 0.3 mg of GUD was emulsified with 3 ml of Freund's incomplete adjuvant, and was injected subcutaneously into several sites on the back of each New Zealand white rabbit. The rabbits were boosted 4 times at 3-week intervals in the same manner, and 7 days after the final injection blood was collected from the ear vein. The specificity of the antisera was tested by Ouchterlony double diffusion. (22), while the titer of the antisera was determined by an enzyme-linked immunosorbent assay using microtiter plates coated with GUD (10 µg/ml). Following the addition of diluted antisera, protein A-horseradish peroxidase conjugate was used to develop the signal of antigen-antibody reaction, and o-phenylenediamine was used to develop the signal (23). After priming and 4 booster injections, the titers of the antisera from rabbits were found to be around $10^7$ as determined by the enzyme-linked immunosorbent assay. The antisera were specific to GUD as only one precipitation line was found in the Ouchterlony double diffusion test (FIG. 1).

The immunoglobulin G (IgG) fraction of the antisera was purified by diethylaminoethyl (DEAE) ion-exchange chromatography (24), and was further purified by affinity chromatography. For affinity purification of anti-GUD, the DEAE-purified IgG solution was passed through a column (1×12 cm) packed with Sepharose 4B gel (Pharmacia LKB Biotechnology, Uppsala, Sweden) coupled with partial purified GUD according to the previous procedures (25). The specific antibodies against GUD were eluted with 0.1M glycine-HCl buffer, pH 2.6, and immediately neutralized with 1M Tris-HCl buffer, pH 8.5.

Enzyme Capture Assay

Wells of microtiter plates (MicroFluor, Dynatech, Alexandria, Va., USA) were coated with 0.1 ml of affinity-purified anti-GUD (10 µg/ml, in 0.1M carbonate buffer, pH 9.6) at 37° C. for 2 hours. The plates were washed 5 times with 10 mM phosphate-buffered saline, pH 7.2, containing 0.05% Tween 20 (PBST) and blocked with 1% bovine serum albumin for 1 hour at room temperature. After PBST washing, 0.1 ml of serial diluted GUD solution (0–100 ng/ml) or cell lysate was added to the wells and incubated at 37° C. for 1.5 hours. The plates were washed 5 times with PBST, and 0.1 ml of MUG solution (200 µg/ml, in PBS) was added to the wells. The plates were incubated at 37° C. for 1.5 hours, and 0.1 ml of 0.2N NaOH was added to each well to stop the enzyme reaction. For negative control, instead of GUD, 0.1 ml of PBS was added into the wells and incubated under the same condition. The results were read with a MicroFluor reader (Dynatech, Alexandria, Va., USA) at a wavelength of 365 nm. A reading of relative fluorescence units larger than the negative control plus three standard deviations was considered positive.

After 24-hour growth of pure strains (or blood cultures positive for gram-negative bacteria) in the BECTEC NR vials, 0.5 ml of the culture broth was aseptically drawn to a microcentrifuge tube, and centrifuged at 5,000×g for 10 min. The cell pellet was lysed at 35° C. for 20 min in 0.5 ml of 0.1M phosphate buffer containing 8% (w/v) sucrose, 25 mM EDTA, 0.05% Triton X-100 and lysozyme (Sigma, 1.2 mg/ml), pH 7.0. The lysate was then used for ECA.

Induction of GUD

Since GUD is an inducible enzyme (21), four β-D-glucuronides were compared for their abilities to induce the enzyme in two strains of *E. coli* (05-8 and CCRC 10316). For this purpose, after the addition of 0.5 ml of the bacterial suspension and 3 ml of blood to the BACTEC NR6A vial, 0.1 ml of a stock solution (16.5 mg/ml, 5-bromo-4-chloro-3-indolyl-β-D-glucuronide, methyl-β-D-glucuronide, 4-methylumbelliferyl-β-D-glucuronide, or p-nitrophenyl-β-D-glucuronide, all from Sigma, St. Louis, Mo., USA) was added to each culture vial to reach a final concentration of 50 µg/ml. The culture vials were then incubated at 35° C. for 24 hours before performing the ECA.

Figure 3:
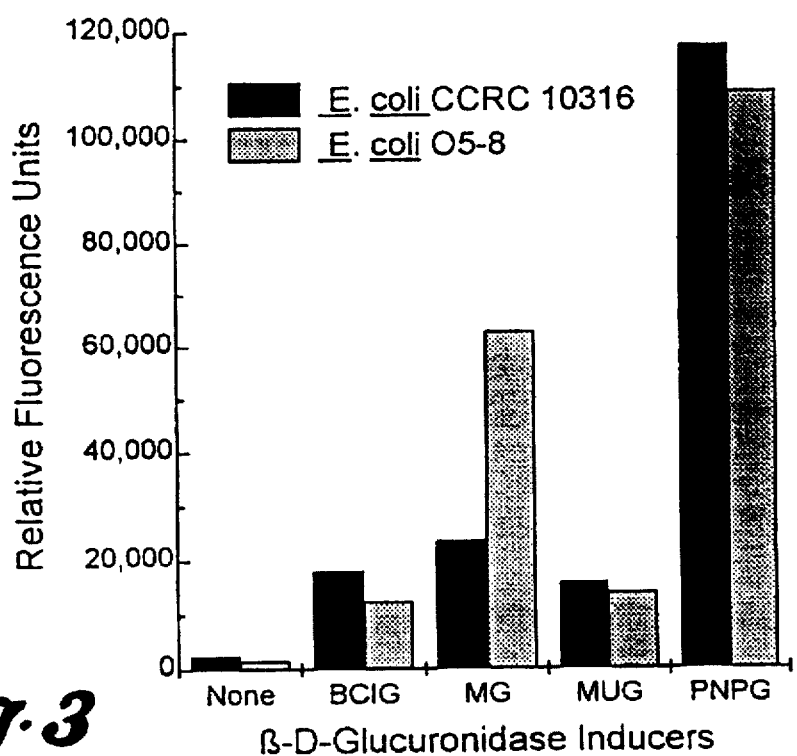
FIG. 3 shows the induction of β-D-glucoronidase by 5-bromo-4-chloro-3-indolyl-β-D-glucuronide (BCIG), methyl-β-D-glucuronide (MG), 4-methylumbelliferyl-β-D-glucuronide (MUG) and p-nitrophenyl-β-D-glucuronide (PNPG) in *E. coli* CCRC 10316 and 05-8. The BACTEC NR6A blood culture vial was supplemented with the different inducers at a final concentration of 50 µg/ml. After the inoculation of *E. coli* and incubation at 35° C. for 24 hours, the culture broth was tested for the activity of β-D-glucuronidase by an enzyme-capture assay. *E. coli* CCRC 10316 and 05-8 had relative fluorescence units of 2,600 and 1,700, respectively, when no inducer was added to the culture vial.

Although most strains of *E. coli* can produce GUD in the BACTEC vials without added inducers, the activity of GUD detected was about 5–64 times higher in the presence of different inducers (FIG. 3). Both *E. coli* CCRC 10316 and 05-8 were induced to approximately the same extent by each of the 4 glucuronides. However, p-nitrophenyl-β-D-glucuronide was found to be the best inducer among the four compounds tested. The captured enzyme activity was 45 and 64 times higher in *E. coli* CCRC 10316 and 05-8, respectively, in the presence of the compound than those vials without any inducer added. Methyl-β-D-glucuronide was the second effective inducer among the four glucuronides tested.

Detection Limit of *E. coli*

To determine the minimal cell number of *E. coli* in the blood culture vials to give a positive ECA result, 3 ml of blood and 0.1 ml of a diluted suspension of *E. coli* (05-8 and CCRC 10316) were injected into the BECTEC NR6A bottle in the presence or absence of p-nitrophenyl-β-D-glucuronide (50 µg/ml) to reach an inoculum level of about 10 CFU/ml. The vials were incubated at 35° C., sampled at intervals to determine the cell numbers, and tested for GUD activity by ECA. For microtiter plates coated with affinity-purified anti-GUD, the detection limit of GUD by ECA was about 0.1 ng/ml ($3\times10^{-13}$M, based on a mol wt of 296,000 of GUD) (26). This enzyme concentration was equal to a cell density of about $10^6$ CFU/ml of *E. coli* as determined in the inoculation experiments without any inducer. The detection limit of *E. coli* was one order lower ($10^5$ CFU/ml) if the inducer p-nitrophenyl-β-D-glucuronide (50 µg/ml) was included in the blood culture vials. The assay was about 5–10 times less sensitive if ion-exchange-purified anti-GUD was used for plate coating.

Clinical Specimens

The blood specimens were collected at the National Cheng-Kung University Hospital. The BACTEC NR6A vials (for aerobic cultures) and BECTEC NR7A (for anaerobic cultures) were normally inoculated with 3–5 ml of blood from the patients, inserted into the BACTEC NR660 instrument (Johnson Laboratories Inc., Towson, Md., USA) and incubated at 35° C. The instrument analyzed the head space gas for $CO_2$ and, if a threshold level is exceeded (Growth Value 25–30 or a change of Growth Value >10–15 between two consecutive readings), indicated that the vial was positive. Sometimes growth in the vial was evident (e.g. turbidity, gas production, or hemolysis) by visual inspection. Positive vials were Gram-stained and subcultured on MacConkey, chocolate, and blood agar plates. All isolates were identified and speciated by standard microbiological techniques. Only those vials showing growth of gram-negative bacteria were tested by ECA according to the procedures described above.

Sensitivity and Specificity

Sensitivity (27) was defined as the number of true positives of ECA divided by the total number of blood cultures from which *E. coli* was isolated by the conventional culture methods. Specificity (27) was defined as the number of true negatives of ECA divided by the total number of blood cultures from which bacteria other than *E. coli* were isolated by the conventional methods.

Of 212 blood cultures showed growth of gram-negative bacteria, 77 were found to contain *E. coli* by the conventional culture methods and among them, 73 were positive by ECA (Table 2). Enzyme-capture assay produced 4 false-negatives (Table 2). Among the 4 false-negatives, 3 were polymicrobial infections with the *E. coli* isolates being GUD-positive as determined by the conventional culture method (11). The fourth false-negative was a blood sample from which only *E. coli* was isolated and this isolate was further confirmed to be GUD-negative. Among the 135 blood specimens from which *E. coli* was not isolated, ECA gave one false-positive (*Salmonella enteritidis*) reaction. Therefore, the sensitivity of ECA for detecting *E. coli* in blood cultures was 94.8% (73/77), and the specificity of ECA was 99.3% (134/135). The agreement between the conventional culture methods and ECA was 97.6% (207/212).

TABLE 2

Results of enzyme-capture assay (ECA) versus conventional culture method for the identification of *E. coli* in blood cultures

| Conventional culture method | No. of results of ECA* | |
|---|---|---|
| | Positive | Negative |
| Positive | 73 | 4 |
| Negative | 1 | 134 |

*In comparison with the conventional culture method, ECA had a sensitivity of 94.8% (73/77) and a specificity of 99.3% (134/135).

The above embodiments and examples illustrate the scope and spirit of the present invention. These embodiments and examples will make apparent to those skilled in the art other embodiments and examples within the scope of the present invention. Therefore, the present invention should be limited only by the appended claims.

LITERATURE CITED

1. Weinstein, M. P., J. R. Murphy, L. B. Reller, and K. A. Lichtenstein. 1983. The clinical significance of positive blood cultures: a comprehensive analysis of 500 episodes of bacteremia and fungemia in adults. II. Clinical observations, with special reference to factors influencing prognosis. Rev. Infect. Dis. 5:54–70.

2. Brauner, A., B. Kaijser, B. Wretlind, and L Khn. 1991. Characterization of *Escherichia coli* isolated in blood, urine and faeces from bacteremic patients and possible spread of infection. Acta Pathol. Microbiol. Immunol. Scand. 99:381–386.

3. Filice, G. A., L. L. Van Etta, C. P. Darby, and D. W. Fraser. 1986. Bacteremia in Charleston County, South Carolina. Am. J. Epdemiol. 123:128–136.

4. Ljungman, P., A. S. Maimborg, B. Nystrm, and A. Tillegrd. 1984. Bacteremia in a Swedish university hospital: a one-year prospective study in 1981 and a comparison with 1975–76. Infection 12:243–247.

5. McGowan, J. E. 1985. Changing etiology of nosocomial bacteremia and fungemia and other hospital acquired infections. Rev. Infect. Dis. 7:S357–S370.

6. Roberts, F. J. 1980. A review of positive blood cultures: identification and source of microorganisms and patterns of sensitivity to antibiotics. Rev. Infec. Dis. 2:329–339.

7. Chiang, T. M., and T. Y. Chang. 1991. Pediatric bacteremia strains grow in blood culture media. Chin. Med. J. (Taipei) 47:39–44.

8. Weinstein, M. P., L. B. Reller., J. R. Murphy, and K. A. Lichtenstein. 1983. The clinical significance of positive blood cultures: a comprehensive analysis of 500 episodes of bacteremia and fungemia in adults. I. Laboratory and epidemiologic observations, Rev. Infect. Dis. 5:35–53.

9. Kilian, M., and P. Bülow. 1976. Rapid diagnosis of Enterobacteriaceae. I. Detection of bacterial glycosidases. Acta Pathol. Microbiol. Scand. Sect. B. 84:245–251.

10. Delisle, G. J., and A Ley. 1989. Rapid detection of *Escherichia coli* in urine samples by a new chromogenic β-glucuronidase assay. J. Clin. Microbiol. 27:778–779.

11. Feng, P. and P. A. Hartman. 1982. Fluorogenic assays for immediate confirmation of *Escherichia coli*. Appl. Environ. Microbiol. 43:1320–1329.

12. Heizmann, W., P. C. Dller, B. Gutbrod, and H. Werner, 1988. Rapid identification of *Escherichia coli* by Fluorocult media and positive indole reaction. J. Clin. Microbiol. 26:2682–2684.

13. Kaspar, C. W. , P. A. Hartman, and A. K. Benson. 1987. Coagglutination and enzyme capture tests for detection of *Escherichia coli* β-galactosidase, β-glucuronidase, and glutamate decarboxylase. Appl. Environ. Microbiol. 53:1073–1077.

14. Trepeta, R. W., and S. C. Edberg. 1984. Methylumbelliferyl-β-D-glucuronide-based medium for rapid isolation and identification of *Escherichia coli*. J. Clin. Microbiol. 19:172–174.

15. Holt, S. M., P. A. Hartman, and C. W. Kaspar. 1989. Enzyme-capture assay for rapid detection of *Escherichia coli* in oysters. Appl. Environ. Microbiol. 55:229–232.

16. Moberg, L. H. 1985. Fluorogenic assay for rapid detection of *Escherichia coli* in food. Appl. Environ. Microbiol. 50: 1383–1387.

17. Robison, B. J. 1984. Evaluation of a fluorogenic assay for detection of *Escherichia coli* in foods. Appl. Environ. Microbiol. 48:285–288.

18. Husson, M. O., C. Mielcarek, D. Izard, and H. Leclerc. 1989. Alkaline phosphatase capture test for the rapid identification of *Escherichia coli* and Shigella species based on a specific monoclonal antibody. J. Clin. Microbiol. 27:1518–1521.

19. Weintraub, M., and S. Raymond. 1963. Antiserums prepared with acrylamide gel used as adjuvant. Science 142:1677–1678.

20. Speer, C. P., D. Hauptmann, P. Stubbe, and Gahr. 1985. Neonatal septicemia and meningitis in Göttingen, West Germany. Pediatr. Infect. Dis. 4:36–41.

21. Novel, G., M. L. Didier-Fichet, and F. Stoeber. 1974. Inducibility of β-glucuronidase in wild-type and hexuronate-negative mutants of Escherichia coli K-12. J. Bacteriol. 120:89–95.

22. Ouchterlony O. 1949. Antigen antibody reactions in gels. Acta Pathol. Microbiol. Scand. 26:507–515.

23. Chang, T. C., C. H. Cheng, and H. C. Chen. 1994. A latex agglutination test for the rapid identification of Vibrio parahaemolyticus. J. Food Prot. 57:31–36.

24. Linn, T. G., A. L. Greenleaf, R. G. Shorenstein, and R. Losick. 1973. Loss of the sigma activity of RNA polymerase of Bacillus subtilis during sporulation. Proc. Natl. Acad. Sci. USA. 70:1865–1869.

25. Hudson, L., and F. C. Hay. 1989. Affinity techniques for molecules and cells. p. 322–329. In Practical immunology. 3rd ed. Blackwell Scientific Publications, London.

26. Blanco, C., and G. Nemoz. 1987. One step purification of Escherichia coli β-glucuronidase. Biochimie 69:157–161.

27. McClure, F. D. 1990. Design and analysis of quantitative collaborative studies: minimum collaborative program. J. Assoc. Off. Anal. Chem. 73:953–960.

What is claimed is:

1. A method for determining the presence of Escherichia coli (E. coli) in a sample comprising the steps of culturing the sample at about 35° C. for about 24 hours in the presence of an E. coli β-D-glucuronidase inducer p-nitrophenyl-β-D-glucuronide; preparing a cell lysate from said cultured sample; contacting said lysate with an immobilized antibody against β-D-glucuronidase of E. coli to bind any E. coli β-D-glucuronidase in said lysate; and detecting any β-D-glucuronidase bound to said immobilized antibody with a β-D-glucuronidase substrate; whereby transformation of said substrate indicates the presence of E. coli in the sample.

2. The method according to claim 1, wherein said substrate is β-D-glucuronide or its derivative.

3. The method according to claim 2, wherein said substrate is 4-methylumbelliferyl-β-D-glucuronide.

4. The method according to claim 1, wherein said antibody is coated on a solid phase.

5. The method according to claim 4, wherein said antibody is coated on a microtiter plate.

6. The method according to claim 4, wherein said substrate is β-D-glucuronide or its derivative.

7. The method according to claim 6, wherein said substrate is 4-methylumbelliferyl-β-D-glucuronide.

8. The method according to claim 5, wherein said substrate is β-D-glucuronide or its derivative.

9. The method according to claim 8, wherein said substrate is 4-methylumbelliferyl-β-D-glucuronide.

* * * * *